United States Patent [19]

Barkenhagen

[11] Patent Number: 5,553,617
[45] Date of Patent: Sep. 10, 1996

[54] NONINVASIVE METHOD AND APPARATUS FOR DETERMINING BODY CHEMISTRY

[75] Inventor: Michael E. Barkenhagen, Norco, Calif.

[73] Assignee: Hughes Aircraft Company, Los Angeles, Calif.

[21] Appl. No.: 375,742

[22] Filed: Jan. 20, 1995

[51] Int. Cl.$^6$ .................................................. A61B 3/10
[52] U.S. Cl. ........................... 128/633; 128/665; 128/745
[58] Field of Search ..................................... 128/633, 664, 128/665, 745

[56] References Cited

U.S. PATENT DOCUMENTS

| | | | |
|---|---|---|---|
| 4,569,354 | 2/1986 | Shapiro et al. | 128/665 |
| 4,811,739 | 3/1989 | Silver | 128/664 |
| 4,836,207 | 6/1989 | Bursell et al. | 128/633 |
| 5,048,946 | 9/1991 | Sklar et al. | 128/633 |
| 5,207,668 | 5/1993 | L'Esperance, Jr. | 606/5 |
| 5,258,788 | 11/1993 | Furuya | 128/633 |
| 5,297,554 | 3/1994 | Glynn et al. | 128/665 |
| 5,323,775 | 6/1994 | Joshi et al. | 128/633 |
| 5,361,758 | 11/1994 | Hall et al. | 128/633 |
| 5,433,197 | 7/1995 | Stark | 128/633 |

OTHER PUBLICATIONS

Radiant Energy and the Eye; Sidney Lerman, M.D.; Professor of Ophthalmology, Emory University School of Medicine, Atlanta; Adjunct Professor of Chemistry, Georgia Institute of Technology, Alanta pp. 177–179.

W. F. Ulrich, et al., *Analytical Instrumentation in the Forensic Sciences*, Beckman Instruments, Inc. (1971) entire document.

G. T. Elerding, et al., Wedge Imaging Spectrometer: Application to Drug and Pollution Law Enforcement, *SPIE–Surveillance Technologies*, vol. 1479 (1991), pp. 380–392.

Anon., Spectrometer Zeros in on Illegal Drugs Remotely, *Applied Optics*, (1992), p. 20.

C. K. Hitzenberger, "Measurement of Corneal Thickness by Low–Coherence Interferometry," *Applied Optics*, vol. 31, No. 31, (Nov. 1993), pp. 6637–6642.

L. K. Marquardt, et al., "Near–Infrared Spectroscopic Measurement of Glucose in a Protein Matrix," *Analytical Chemistry*, vol. 65, No. 22, pp. 3271–3278.

Anon., "New Cholesterol Test Could be Part of Routine Eye Exam," *AOA News*, (Mar. 15, 1994), p. 8.

*Primary Examiner*—Angela D. Sykes
*Assistant Examiner*—Eric F. Winakur
*Attorney, Agent, or Firm*—G. S. Grunebach; M. W. Sales; W. K. Denson-Low

[57] ABSTRACT

The body chemistry of a person is determined by directing a beam of light into the eye of the person, measuring the spectral response of the eye to the beam of light, comparing the measured spectral response to a standard spectral response, and forming a conclusion as to the chemistry of the body from the comparison. The light selected for the measurement does not harm the eye, and is preferably in the ultraviolet or infrared ranges. The response of the eye chosen for measurement is that of reflected, fluoresced, or scattered light. It is preferred to use two or more of these techniques simultaneously, to minimize the likelihood of error. The comparison is made by comparing the measured response of the eye to a standard response from a library of previously established responses.

20 Claims, 4 Drawing Sheets

NONINVASIVE METHOD AND APPARATUS FOR DETERMINING BODY CHEMISTRY

BACKGROUND OF THE INVENTION

This invention relates to the noninvasive measurement of body chemistry, and, more particularly, to the measurement of body chemistry using the response to light of externally accessible portions of the body.

The measurement of body chemistry is important in medicine, law enforcement, safety practice, and other fields. Body chemistry has traditionally been determined by obtaining fluid from the body, typically blood, urine, spinal fluid, and the like. A wet or spectral chemical analysis of the fluid is made and evaluated for the chemical content of the fluid.

In recent years, the effects of the use of illegal drugs such as narcotics and the excessive use of legal drugs such as alcohol have become important concerns for employers and others who may be affected by a person under the influence of such drugs. Drug testing programs, such as mandated testing for all prospective employees and random testing for persons in safety-sensitive positions, have become commonplace. Such testing is accomplished by obtaining fluid from the body and analyzing it as discussed previously. Apart from any question of legality of the testing, such testing is time consuming, expensive, invasive, and can cause physical discomfort or anxiety to some degree in those tested. The testing can also fail to achieve its desired objectives in some cases, as for example when a person has previously passed drug testing and thereafter uses an illegal drug shortly before performing a safety-sensitive function.

The majority of persons do not use drugs in an unacceptable manner. Invasive testing is, for those persons, a necessary burden both for those doing the testing and for the person tested. It would therefore be particularly desirable to have a reliable preliminary screening test to assess whether there was any reason to perform full quantitative testing in each case.

There is a need for an improved approach to determining body chemistry, such as the presence of drugs. Such an approach would desirably provide both a current state of body chemistry and information on the historical use of drugs, at least in a qualitative sen se. The approach would also desirably be noninvasive, painless, and fast so as to reduce any burden associated with the testing. The present invention fulfills this need, and further provides related advantages.

SUMMARY OF THE INVENTION

The present invention provides a method and apparatus for performing a noninvasive determination of the body chemistry of a subject. The approach is versatile, and may be directed at those elements of body chemistry associated with body function and health, or those elements of body chemistry associated with the use or abuse of drugs, alcohol, and the like. The determination is performed quickly, without harm or physical discomfort to the subject, and without introducing any chemicals into the environment.

In accordance with the invention, a method for determining body chemistry comprises the steps of generating an input beam of light of a wavelength and intensity not harmful to an eye of a subject, directing the input beam of light into the eye of the subject, the step of directing being performed in vivo, and measuring a response, such as a spectral, scattering, or fluorescence response, of the eye to the input beam of light. The method further includes providing a standard spectral response of a chemical state of the eye to the input beam of light, comparing the measured spectral response to the standard spectral response, and forming a conclusion as to the body chemistry of the person from the comparison made in the step of comparing.

Measurements of body chemistry from the eye are useful because the eye is externally accessible and is physiologically insensitive to moderate intensities of particular wavelengths of light that can be easily generated and analyzed. Ultraviolet and infrared light are of particular interest for such determinations. Moreover, various regions of the eye have fluids therein whose composition changes either rapidly or slowly over time. Noninvasive measurements of the chemistry in these regions permits the body chemistry to be ascertained both for short-term and long-term effects.

In a preferred embodiment, multiple determinations of body chemistry are made simultaneously using the approach outlined above and separate light-based techniques. Thus, for example, obtaining reflectance, fluorescence, and scattering information at the same time, and at the same or different wavelengths, permits independent assessments of the body chemistry. Multiple determinations also allows logic to be applied in identifying various conditions such as false positive readings and abnormal responses to one type of test.

In accordance with the preferred embodiment, a method for determining body chemistry comprises the steps of generating an input beam of light of a wavelength and intensity not harmful to an eye of a subject, directing the input beam of light into the eye of the subject, the step of directing being performed in vivo, first measuring a first type of spectral response of the eye to the input beam of light, and second measuring a second type of response of the eye to the input beam of light. A first type and a second type of standard response of the eye to the input beam of light are provided, preferably in the form of a library of responses for various types of conditions and chemistries. The method further includes first comparing the measured first type of spectral response to the standard first type of response, second comparing the measured second type of response to the standard second type of response, and forming a conclusion as to the body chemistry of the person from the comparisons made in the steps of first and second comparing.

The present invention provides an advance in the art of determining the chemistry of the body. The method is fast, both in terms of requiring only a brief measuring period and also in terms of yielding the results quickly, and is noninvasive. Other features and advantages of the present invention will be apparent from the following more detailed description of the preferred embodiment, taken in conjunction with the accompanying drawings, which illustrate, by way of example, the principles of the invention.

DETAILED DESCRIPTION OF THE INVENTION

Figure 1:
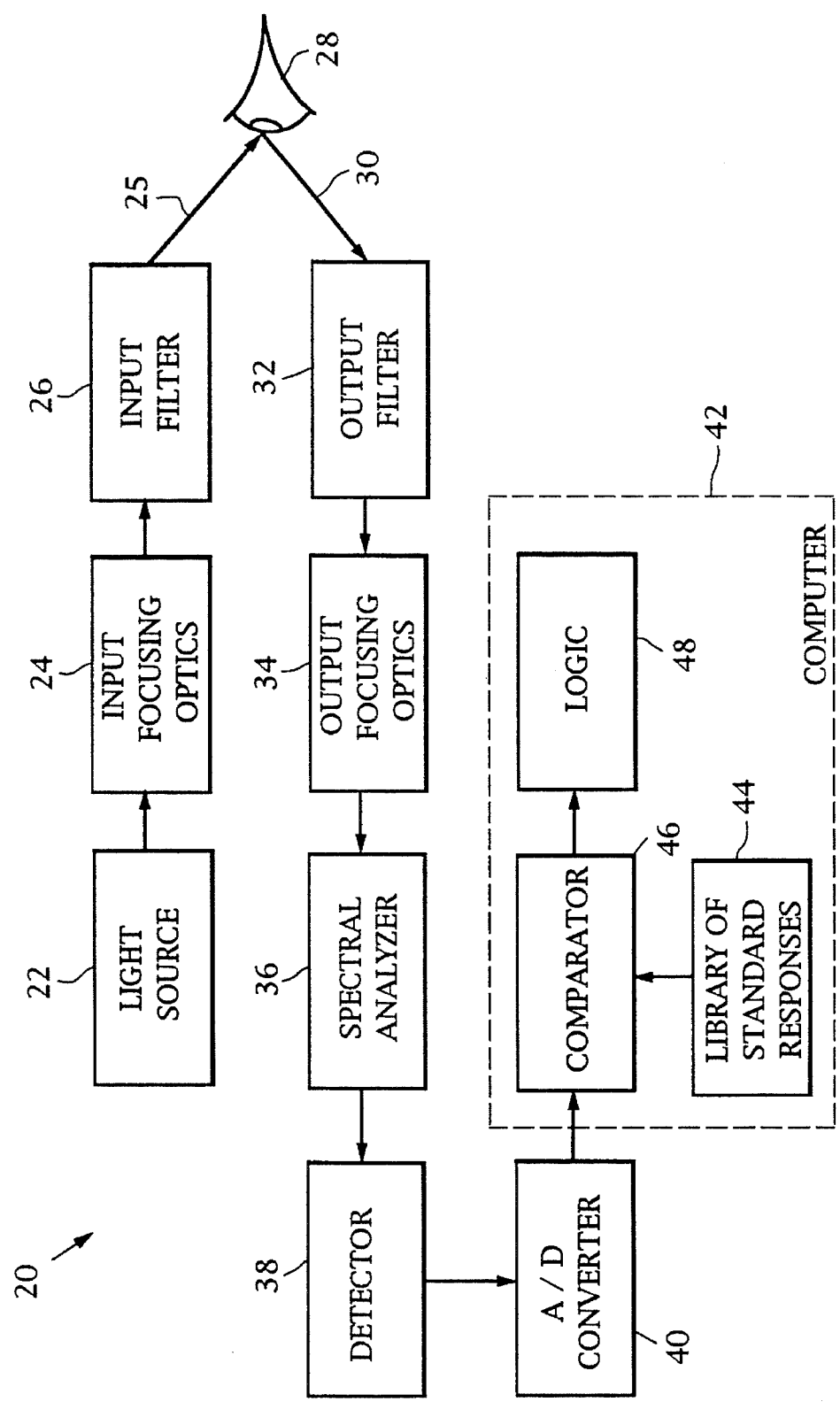
FIG. 1 is a schematic illustration of an apparatus according to the invention.
Figure 2:
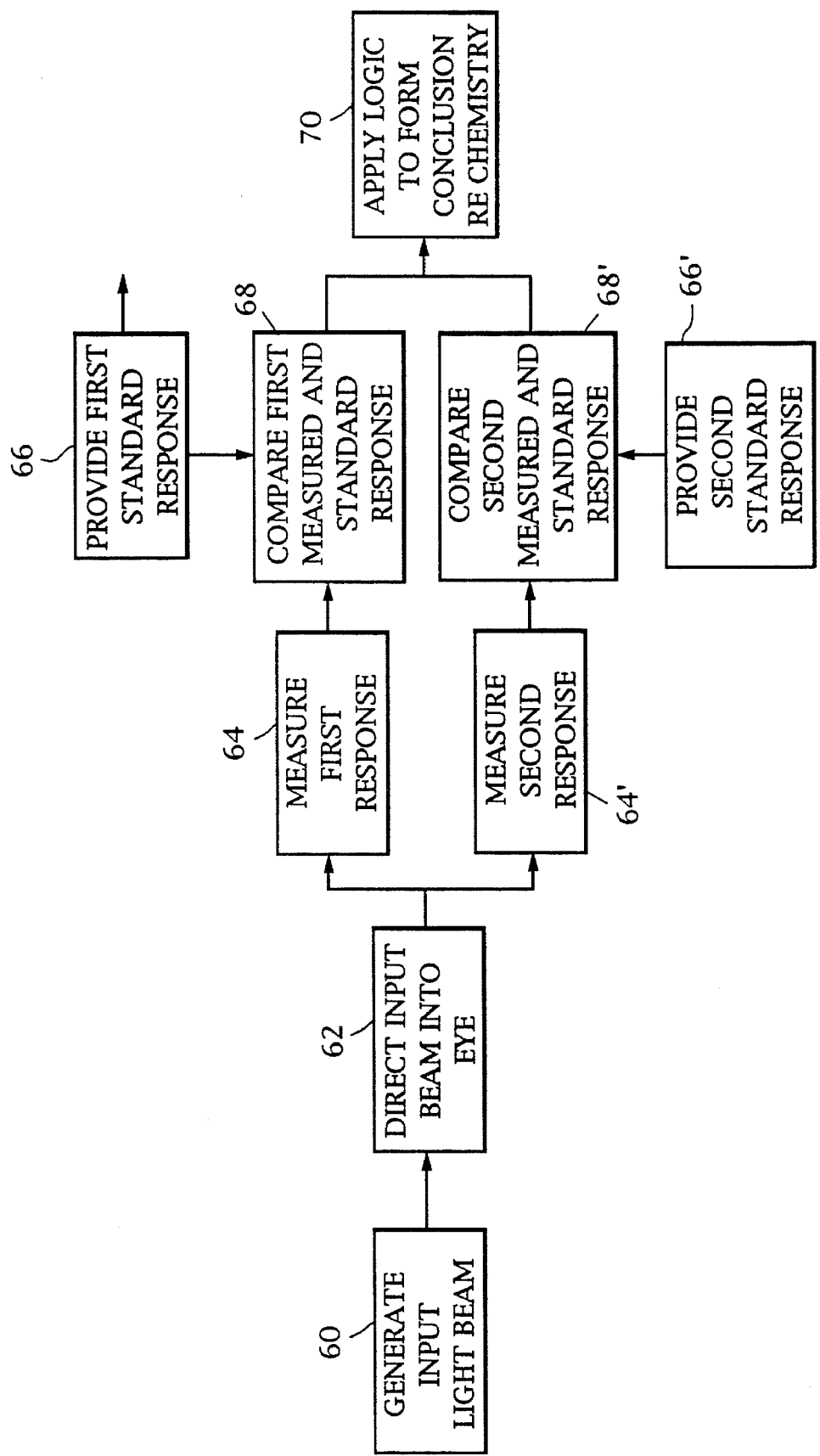
FIG. 2 is a block diagram for practicing one embodiment of the method of the invention.

FIG. 1 schematically depicts a preferred apparatus 20 according to the invention, and FIG. 2 shows the related method for practicing the invention using this apparatus 20. A light source 22 generates light that is used in the chemical analysis procedure, numeral 60. The light is of a wavelength and intensity that will not damage the eye, and, preferably, is not detected by the unaided eye. The light produced by the light source 22 is preferably at a wavelength of from about 200 to about 300 nanometers, in the ultraviolet range, and/or from about 700 to about 800 nanometers, in the near-infrared range. Light in both of these ranges is substantially undetected by the human eye, and does not damage the eye as long as the intensity is not so high or the duration of exposure so long that the light will damage the tissue.

Input focusing optics 24 directs an input beam 25 into the eye, numeral 62. The input focusing optics 24 is of a conventional type using lenses and mirrors, and may be adjustable to focus the light at specific locations within the eye, as will be discussed subsequently. An input filter 26 may also be provided to select specific wavelengths for introduction into the eye, inasmuch as the light source 22 may produce light of a bandwidth broader than that ultimately desired. Care is taken not to introduce a higher intensity or longer duration of light into the eye than required.

The focused and filtered input beam of light 25 is introduced into an eye 28 of a subject. The present invention is noninvasive except for this introduced beam, which is desirably not visible to the eye and does not harm the eye. (The term "noninvasive" as used herein means that there is no physical invasion of the body, but that introduction of a beam of light into the eye is permitted.) This chemical analysis is preferably accomplished in vivo, that is, with a live subject.

An output beam of light 30 is emitted from the eye 28 responsive to the stimulus of the input beam 25. The output beam 30 can be produced by various mechanisms within the eye, which will be discussed subsequently. The output beam 30 is optionally filtered by an output filter 32 if it is expected to contain wavelengths not of interest to the analysis. The output beam 30 passes through output focusing optics 34 of a conventional type to focus the output beam 30. At this point, the output beam 30 constitutes a single broadband beam. A spectral analyzer 36 breaks the output beam 30 into its component spectrum. The spectral analyzer 36 is desirably a prism, a diffraction grating, or a ruled grating.

The output focusing optics 34 is selected to focus the spectrally analyzed beam 36 onto a detector 38 having a bandwidth sufficient to encompass the wavelengths required for the subsequent analysis. The detector 38 receives as an input the filtered, focused, and analyzed output beam 30 and produces as an output an electrical signal indicative of the intensity of the input beam as a function of wavelength, termed a measured spectral response. If the detector 38 produces the measured spectral response in analog form and the subsequent procedures are to be performed digitally, as is preferably the case, an analog-to-digital (A/D) converter 40 provided to make the conversion of the spectral response to digital form. On the other hand, if the output of the detector 38 is digital, as in the case of a charge-coupled diode array, then the A/D converter 40 would not be necessary.

The detector 38 can be a single detector or more that one detector for specific wavelengths. In the preferred embodiment, more than one response is analyzed. At least one of the responses is a spectral response a selected wavelength range, and the other responses are typically either spectral responses in other wavelength ranges, fluorescence responses in a selected wavelength range, or scattering responses in a selected wavelength range. If these responses utilize, for example, both the ultraviolet and infrared wavelength ranges, separate detectors 38 for these ranges would ordinarily be provided. A beam splitter can be provided to direct components of the output beam to these detectors. The apparatus 32, 34, 36, 38, and 40 are collectively described as measuring a first response, numeral 64, and, where provided, a second response, numeral 64'.

The chemical analyses of the one or more responses are performed using the digital processing capabilities of a computer 42 and a library 44 of standard response(s) stored in the computer.

Figure 3A:
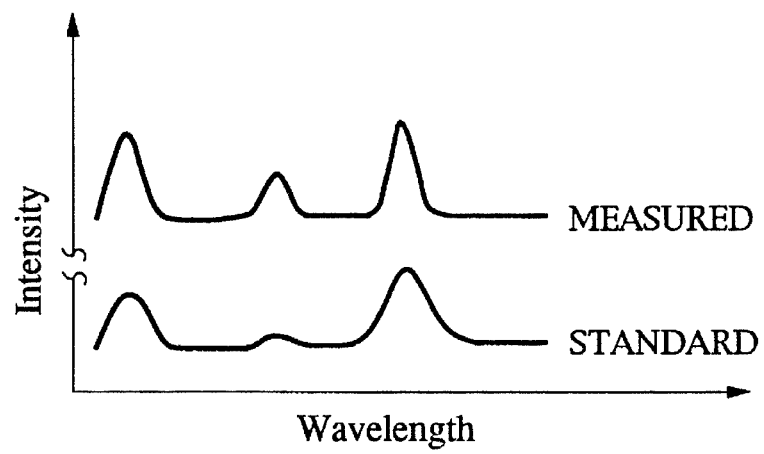
FIGS. 3($a$) and 3 ($b$) are idealized depictions of two sets of interrelations between the measured and standard spectral responses of the eye.
Figure 3B:
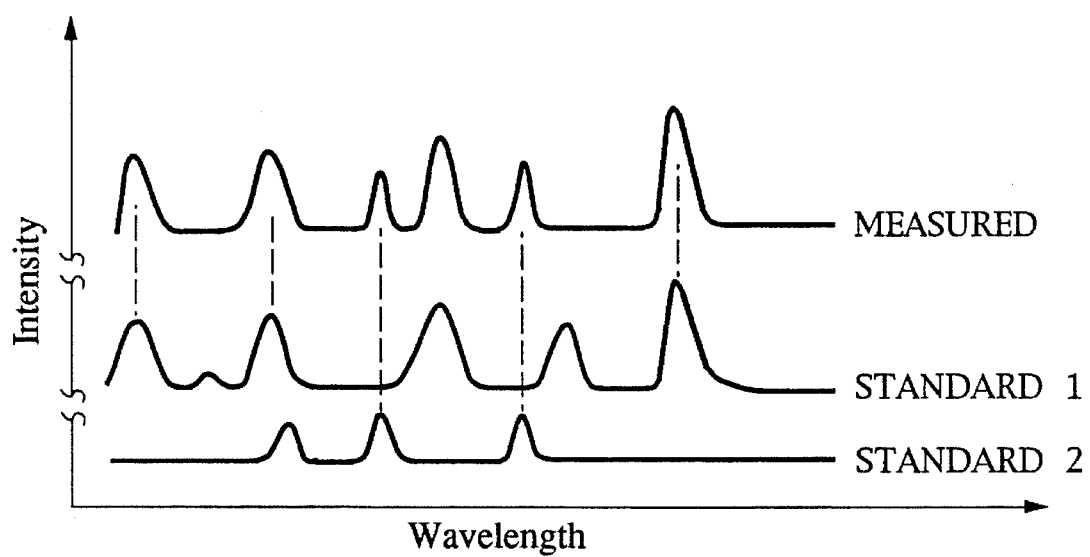

The measured spectral response can be characterized in various ways. Most commonly, the is a curve spectral response of intensity as a function of wavelength, as depicted in FIGS. 3(a) and 3(b). Such a curve typically exhibits peaks indicative of the chemical composition of the region of the eye 28 in which the input beam 25 interacts with the liquid inside the eye to produce the output beam The spectral response of this type can therefore be alternatively characterized by the wavelengths of the peaks found in the spectrum.

Standard spectral responses for various possible chemical constituents of the body are provided, numeral 66 (and, where appropriate, 66'). These standard spectral responses are, in many cases, available in reference works. If not, a standard spectral response can be developed by preparing a simulated subject eye having a fluid therein which contains a known chemical of interest in a known concentration. The apparatus 20 is used to measure the spectral response of this known standard, which then becomes part of the standard spectral response library for subsequent measurements of unknowns. The present approach can be used with just a single standard response in the library of each type of spectral response, if there is an interest in analyzing for just one chemical type. On the other hand, in the drug-screening application, a number of standard spectral responses—each corresponding to the response characteristic of an illegal drug—is provided in the library. The screening for multiple chemicals requires no further testing of the subject, only additional repetitions of the computer matching operation.

The measured spectral response, provided from the detector 98, and the standard spectral response for a particular chemical, provided from the library, are compared, numeral 68 (and 68') by a comparator function 46 in the computer 42. Many analog and digital techniques for comparing two curves for a goodness of correlation are available, and any of these techniques can be used. In the preferred approach, the comparison is performed digitally. The preferred technique is to prepare a listing of the peaks found in the measured and standard spectral responses, using a cutoff value to differentiate a peak from the background. Then the presence and absence of peaks in the measured and standard spectral responses is compared to find the degree to which the measured spectral response matches to the standard spectral response for each chemical being studied. Thus, the preferred approach involves matching peak locations, rather than peak locations and peak intensities by more-mathematical approaches such as autocorrelation, because of variations in concentration of the chemicals between the measured specimen and the standard.

Once a degree of matching, ranging from none to perfect, of the measured and the standard spectral responses is determined in step 68 is available, logic 48 is applied to form a conclusion as to the presence or absence of the chemical in the subject, numeral 70. At the limits of no or perfect matching, there is no difficulty in determining the absence or presence, respectively, of the chemical used to prepare the standard. In other cases, however, the identification can be more difficult.

FIGS. 3(a) and 3(b) illustrate some of the possible situations. In FIG. 3(a), there is a clear match of two of three peaks, but not a clear match as to the third peak. In a case such as this, it may be useful to have a measured spectral response of an other type, and the preferred embodiment of FIG. 2 provides for the use of multiple types of spectral responses to improve the certainty of identification. In FIG. 3(b), two different standard spectral responses are required to account for all of the peaks of the measured spectral response, suggesting that the chemicals associated with the spectral responses of both standards are present. There can be no generalization as to the analysis of various spectral responses, and each individual case must be handled separately.

At the present time, three types of responses of the eye are contemplated for use with the invention, although the invention is not limited to these three and others can be used. All of these techniques are known to be operable for the detection of chemicals such as drugs, using other types of instrumentation. See, for example, W. F. Ulrich et al., "Analytical Instrumentation in the Forensic Sciences," Beckman Instruments Corp., May 1971.

The first type of analysis is ultraviolet reflection (ultraviolet spectrophotometry) to measure the absorption spectrum. This measurement is conducted with input light of about 200–300 nanometers wavelength and output light of the same wavelength range. The second type of analysis is ultraviolet fluorescence. This measurement is conducted with input light of a specific wavelength within the range of about 200–300 nanometers, and output light and subsequent spectral data curves in the range of 300 nanometers and above, and typically in the range of about 300–500 nanometers. The same ultraviolet light source may be used for both reflection and fluorescence, but the detector has a range of about 200–300 nanometers for reflection and 300–500 nanometers for fluorescence. Many UV reflection and fluorescence spectral response curves are available in the scientific and medical literature.

The third type of spectral analysis is Raman infrared scattering spectroscopy of light in the range of about 700 to about 800 nanometers. Both a different light source 22 and a different detector 38 are ordinarily used for the infrared measurements than for the UV measurements. Light sources and detectors for both the UV and IR ranges are readily available commercially. As in the case of the UV spectroscopy, Raman spectra of various drugs and other chemicals are available in the scientific and medical literature.

Figure 4:
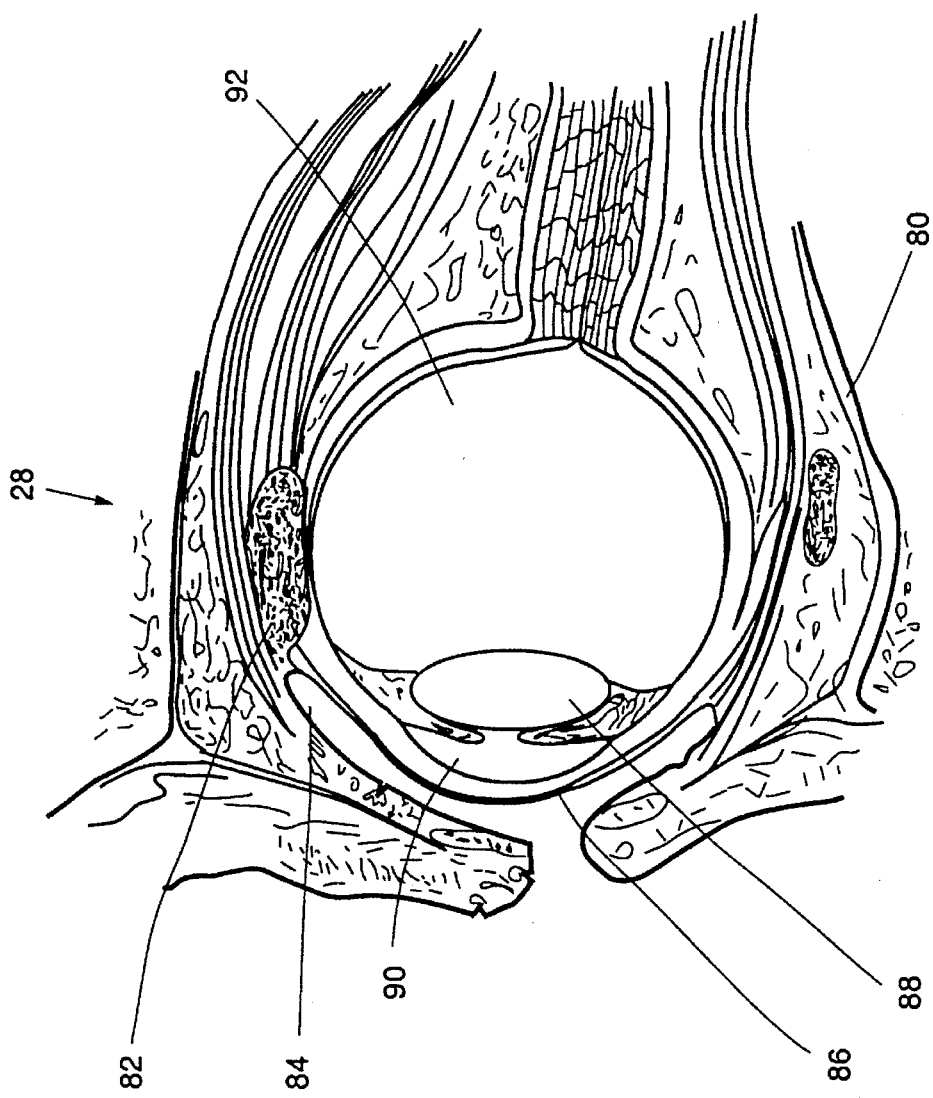
FIG. 4 is a schematic illustration of the eye in cross section, illustrating those parts pertinent to the present invention.

FIG. 4 schematically illustrates that portion of the structure of the human eye which is pertinent to the present invention. The eye 28 is generally, but not perfectly, spherical. It is received in a socket 80 in the skull. Tear glands and ducts 82 in the soft tissue surrounding the socket produce moisture that covers the front surface of the eyeball with a thin film 84 of tears. A cornea 86 lies behind the tear surface of the eye, and a lens 88 is spaced apart behind the cornea. Between the cornea 86 and the lens 88 lies a volume of fluid termed the aqueous humor 90. Behind the lens 88 lies a volume of fluid termed the vitreous humor 92.

There are thus three distinct volumes of fluid associated with the eye 28: the tears 84, the aqueous humor 90, and the vitreous humor 92. The optics 24 and 34 of the present invention are designed to obtain spectral responses from these three areas individually. The advantage to obtaining responses from the areas one at a time is that the fluid in each volume is changed at a different rate by the body. The tears 84 are produced with fluid that changes about every 5–7 minutes. The fluid of the aqueous humor 90 changes about every 1-½ to 2 hours. The fluid of the vitreous humor 92 changes over a matter of days.

An optical response analysis of the tears therefore indicate the current status of a chemical found in the tears. The optical spectral response analysis of the aqueous humor provides a 1-½ to 2 hour average of a chemical found in the fluid of the aqueous humor. The optical spectral response analysis of the vitreous humor provides a longer term average of a chemical found in the fluid of the vitreous humor. The ability to selectively obtain current or time-averaged data on the presence of chemicals from a single test procedure, changing nothing more than the focus of the optical components, is of value to those seeking the presence of drugs in the system of the subject, and also to medical personnel studying normal and abnormal functioning of the body.

The chemical composition of each selected region of the eye can be sampled by controlling the optics 24 and 34 of the apparatus 20, leaving the other elements unchanged. To sample a selected region, the focal lengths of the input focusing optics 24 and the output focusing optics 34 are set to the required values to focus in the selected region of the eye. Responses of the eye are thence the responses of the selected region.

At the present time, the invention is designed for use in a qualitative manner to detect the presence of chemicals that might require further detailed sampling and chemical analysis. The present approach requires only about one second to provide a screening of the subject as to complete absence of a chemical in the fluid of the eye, or the presence of a quantity of the chemical that could require further sampling and analysis to establish an exact quantitative value of the chemical.

The discussion herein has been directed primarily toward the detection of illegal drugs, the principal interest of the inventor. The present invention is not so limited, however. It may be used for medical applications such as sugar in diabetics and chemically based diseases of the eye.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A method for determining body chemistry, comprising the steps of:

generating an input beam of light of a wavelength and intensity not harmful to an eye of a subject;

directing the input beam of light into the eye of the subject;

measuring a spectral response of the eye to the input beam of light due to optical interactions of the input beam with a fluid chemistry of the eye, the response being selected from the group consisting of an ultraviolet reflection spectral response, an ultraviolet fluorescence spectral response, and a Raman scattering response;

providing a standard spectral response of a chemical state of the eye to the input beam of light produced by optical interactions of a light beam with the fluid chemistry of a chemical whose presence in the subject is to be determined, the type of standard response being selected to correspond to the type of response selected in the step of measuring;

comparing the measured response to the standard response; and forming a conclusion as to the body chemistry of the subject from the comparison made in the step of comparing.

2. The method of claim 1, wherein the step of generating includes the step of generating light of a wavelength of from about 200 to about 300 nanometers and from about 700 to about 800 nanometers.

3. The method of claim 1, wherein the step of directing includes the step of focusing the input beam of light to a selected location within the eye.

4. The method of claim 1, wherein the step of directing includes the step of filtering the input beam of light to remove wavelengths that are not within a desired wavelength range.

5. The method of claim 1, wherein the step of measuring includes the step of focusing an output beam of light from the eye upon a spectral detector.

6. The method of claim 5, wherein the step of focusing includes the step of focusing the output beam of light from a layer of a tearing fluid on an external surface of the eye.

7. The method of claim 5, wherein the step of focusing includes the step of focusing the output beam of light from an aqueous humor of the eye.

8. The method of claim 5, wherein the step of focusing includes the step of focusing the output beam of light from a vitreous humor of the eye.

9. The method of claim 1, wherein the step of comparing includes the step of comparing for a presence of spectral lines in a measured spectral response and a standard spectral response.

10. A method for determining body chemistry, comprising the steps of:

generating an input beam of light of a wavelength and intensity not harmful to an eye of a subject, wherein the step of generating includes the step of
generating an input beam having a wavelength of from about 200 to 300 nanometers;

directing the input beam of light into the eye of the subject;

measuring a spectral response of the eye to the input beam of light due to optical interactions of the input beam with a fluid chemistry of the eye, the response being selected from the group consisting of an ultraviolet reflection spectral response, an ultraviolet fluorescence spectral response, and a Raman scattering response;

wherein the step of measuring includes the step of measuring a reflected ultraviolet beam of light;

providing a standard spectral response of a chemical state of the eye to the input beam of light produced by optical interactions of a light beam with the fluid chemistry of a chemical whose presence in the subject is to be determined, the type of standard response being selected to correspond to the type of response selected in the step of measuring;

comparing the measured response to the standard response; and forming a conclusion as to the body chemistry of the subject from the comparison made in the step of comparing.

11. A method for determining body chemistry, comprising the steps of:

generating an input beam of light of a wavelength and intensity not harmful to an eye of a subject, wherein the step of generating includes the step of
generating an input beam having a wavelength of from about 200 to about 300 nanometers;

directing the input beam of light into the eye of the subject;

measuring a spectral response of the eye to the input beam of light due to optical interactions of the input beam with a fluid chemistry of the eye, the response being selected from the group consisting of an ultraviolet reflection spectral response, an ultraviolet fluorescence spectral response, and a Raman scattering response;

wherein the step of measuring includes the step of measuring an ultraviolet fluoresced beam of light;

providing a standard spectral response of a chemical state of the eye to the input beam of light produced by optical interactions of a light beam with the fluid chemistry of a chemical whose presence in the subject is to be determined, the type of standard response being selected to correspond to the type of response selected in the step of measuring;

comparing the measured response to the standard response; and forming a conclusion as to the body chemistry of the subject from the comparison made in the step of comparing.

12. A method for determining body chemistry, comprising the steps of:

generating an input beam of light of a wavelength and intensity not harmful to an eye of a subject, wherein the step of generating includes the step of
generating an input beam having a wavelength of from about 700 to 800 nanometers; and directing the input beam of light into the eye of the subject;

measuring a spectral response of the eye to the input beam of light due to optical interactions of the input beam with a fluid chemistry of the eye, the response being selected from the group consisting of an ultraviolet reflection spectral response, an ultraviolet fluorescence spectral response, and a Raman scattering response;

wherein the step of measuring includes the step of measuring a Raman scattered beam of light;

providing a standard spectral response of a chemical state of the eye to the input beam of light produced by optical interactions of a light beam with the fluid chemistry of a chemical whose presence in the subject is to be determined, the type of standard response being selected to correspond to the type of response selected in the step of measuring;

comparing the measured response to the standard response; and forming a conclusion as to the body chemistry of the subject from the comparison made in the step of comparing.

13. A method for determining body chemistry, comprising the steps of:
generating an input beam of light of a wavelength and intensity not harmful to an eye of a subject;
directing the input beam of light into the eye of the subject;
first measuring the first type of response of the eye to the input beam of light due to optical interactions of the input beam with a fluid chemistry of the eye;
second measuring a second type of response of the eye to the input beam of light due to optical interactions of the input beam with the fluid chemistry of the eye;
first providing a first type of standard response of the eye to the input beam of light due to optical interactions of the input beam with the fluid chemistry of a chemical whose presence in the subject is to be determined;
second providing a second type of standard response of the eye to the input beam of light due to optical interactions of the input beam with the fluid chemistry of the chemical whose presence in the subject is to be determined;
first comparing the measured first type of response to the standard first type of response;
second comparing the measured second type of response to the standard second type of response; and
forming a conclusion as to the body chemistry of the subject from the comparisons made in the steps of first and second comparing.

14. The method of claim 13, wherein the step of first measuring includes the step of
first measuring a response selected from the group consisting of a reflection spectral response, a fluorescence spectral response, and a Raman scattering response.

15. The method of claim 13, wherein the step of second measuring includes the step of
second measuring a response selected from the group consisting of a reflection spectral response, a fluorescence spectral response, and a Raman scattering response.

16. The method of claim 13, wherein the step of generating includes the step of
generating light of a wavelength selected from the group consisting of a wavelength of from about 200 to about 300 nanometers and from about 700 to about 800 nanometers.

17. An apparatus for determining body chemistry, comprising:
a source of an input beam of light of a wavelength and intensity not harmful to an eye of a subject;
means for directing the input beam of light into the eye of the subject;
means for measuring a spectral response of the eye to the input beam of light due to optical interactions of the input beam with a fluid chemistry of the eye;
a source of standard spectral response of a chemical state of the eye to the input beam of light due to optical interactions of the input beam with the fluid chemistry of the eye, for a chemical whose presence in the subject is to be determined;
means for comparing the measured response to the standard response;
means for forming a conclusion as to the body chemistry of the subject from the comparison made by the means for comparing, for the chemical whose presence is to be determined;
means for measuring a second response of the eye to the input beam of light due to optical interactions of the input beam with the fluid chemisrty of the eye,
a source of a standard second response of a chemical state of the eye to the input beam of light due to optical interactions of the input beam with the fluid chemistry of the eye, for the chemical whose presence in the subject is to be determined, and
means for comparing the measured second response to the standard second response; and wherein the means for forming a conclusion includes
means for forming a conclusion as to the body chemistry of the subject from the comparison made by the means for comparing the measured response and the comparison made by the means for comparing the measured second response.

18. A method for determining body chemistry, comprising the steps of:
generating an input beam of light of a wavelength and intensity not harmful to an eye of a subject:
directing the input beam of light into the eye of the subject;
measuring a spectral response of the eye to the input beam of light due to optical interactions of the input beam with a fluid chemistry of the eye, the response being selected from the group consisting of an ultraviolet reflection spectral response, an ultraviolet fluorescence spectral response, and a Raman scattering response, wherein the step of measuring a response of the eye consists of the step of selecting the ultraviolet reflection spectral response;
providing a standard spectral response of a chemical state of the eye to the input beam of light produced by optical interactions of a light beam with the fluid chemistry of a chemical whose presence in the subject is to be determined, the type of standard response being selected to correspond to the type of response selected in the step of measuring;
comparing the measured response to the standard response; and
forming a conclusion as to the body chemistry of the subject from the comparison made in the step of comparing.

19. A method for determining body chemistry comprising the steps of:
generating an input beam of light of a wavelength and intensity not harmful to an eye of a subject;
directing the input beam of light into the eye of the subject;
measuring a spectral response of the eye to the input beam of light due to optical interactions of the input beam with a fluid chemistry of the eye, the response being selected from the group consisting of an ultraviolet reflection spectral response, an ultraviolet fluorescence spectral response, and a Raman scattering response, wherein the step of measuring a response of the eye consists of the step of
selecting the ultraviolet fluorescence spectral response:
providing a standard spectral response of a chemical state of the eye to the input beam of light produced by optical interactions of a light beam with the fluid chemistry of a chemical whose presence in the subject is to be determined, the type of standard response being selected to correspond to the type of response selected in the step of measuring;

comparing the measured response to the standard response; and forming a conclusion as to the body chemistry of the subject from the comparison made in the step of comparing.

20. A method for determining body chemistry, comprising the steps of:

generating an input beam of light of a wavelength and intensity not harmful to an eye of a subject;

directing the input beam of light into the eye of the subject;

measuring a spectral response of the eye to the input beam of light due to optical interactions of the input beam with a fluid chemistry of the eye, the response being selected from the group consisting of an ultraviolet reflection spectral response, an ultraviolet fluorescence spectral response, and a Raman scattering response, wherein the step of measuring a response of the eye consists of the step of selecting the Raman scattering response;

providing a standard spectral response of a chemical state of the eye to the input beam of light produced by optical interactions of a light beam with the fluid chemistry of a chemical whose presence in the subject is to be determined, the type of standard response being selected to correspond to the type of response selected in the step of measuring;

comparing the measured response to the standard response; and forming a conclusion as to the body chemistry of the subject from the comparison made in the step of comparing.

* * * * *